(12) United States Patent
Agee

(10) Patent No.: US 6,261,831 B1
(45) Date of Patent: Jul. 17, 2001

(54) ULTRA-WIDE BAND RF-ENHANCED CHEMOTHERAPY FOR CANCER TREATMEAT

(75) Inventor: Forrest J. Agee, Arlington, VA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/277,596

(22) Filed: Mar. 26, 1999

(51) Int. Cl.[7] ........................................... C12M 1/42
(52) U.S. Cl. ..................... 435/285.2; 607/154; 607/101; 607/74; 606/33; 600/14
(58) Field of Search ..................... 600/2, 14, 411; 607/23, 58, 72, 73, 74, 148, 154, 901, 101; 606/33; 435/285.2; 604/20

(56) References Cited

U.S. PATENT DOCUMENTS 5,386,837 * 2/1995 Sterzer ................................. 128/898
5,501,704 * 3/1996 Chang et al. ........................... 607/69
6,104,959 * 8/2000 Spertell ............................... 607/101

* cited by examiner

*Primary Examiner*—David A. Redding
(74) *Attorney, Agent, or Firm*—Kenneth E. Callahan

(57) ABSTRACT

The ultra-wide band rf-enhanced chemotherapy for treatment of cancer and other intracellular diseases provides for increasing drug effectiveness. It also provides a means of treatment of inoperable cancers. The invention uses ultra-wide band short pulses to provide high electric field strength in diseased areas of a patient to induce electroporosis preferentially in the region to be treated by chemotherapy. The effect is to make the interiors of the cells in the affected region open to the chemotherapeutic agent. The treatment can be enhanced in its effectiveness thereby. It also enables treatment with reduced doses of the therapeutic agent and reduces side effects in other areas of the patient through the reduction of the total dosage. The invention makes specific use of the polarization of UWB fields and the very short duration of the pulsed electromagnetic fields induced into the region to be treated to minimize the absorbed rf energy associated with the treatment, making the heating of tissue negligible. It also uses a pulse repetition frequency slow enough to avoid wholesale killing of cells through osmotic shock.

4 Claims, 2 Drawing Sheets

ULTRA-WIDE BAND RF-ENHANCED CHEMOTHERAPY FOR CANCER TREATMEAT

BACKGROUND OF THE INVENTION

1. Field of the Invention

This invention is in the field of electroporosis, and in particular involves methods for generating electromagnetic fields in the interior of the body to improve delivery of therapeutic drugs to the body's cells.

2. Description of the Prior Art

Electroporosis is the process wherein cell membrane pores are opened through the application of electromagnetic fields. For example, Dr. Diane Gaylor of MIT has demonstrated electroporosis of normal skeletal muscle cells at electric field gradients as low as 2.5 kV per meter.

Inoperable cancers are frequently treated by chemotherapy, ionizing radiation, or combined radiation/chemotherapeutic modalities. A central limitation of chemotherapeutic effectiveness is the inability of the chemical agent to penetrate into the tumor tissue, and especially into the tumor cell, thus resulting in resistance to therapy. Dr. Mir in France has experimentally determined that electroporation of cancer cells can increase the influx of chemotherapeutic agents into those cells by more that 50 fold. He has also demonstrated that this effect appears useful in treatment of human patients with inoperable cancer in cases where electrodes can be placed on the skin on opposite sides of the tumor. In these treatments the patient is pre-loaded with an orally administered chemotherapeutic agent and the locally imposed electromagnetic field is believed to increase tumor uptake of the agent through the process of membrane electroporation.

Other diseases suffer the same difficulty of getting the therapeutic drug to the target site. For example, diseases based on the existence of intracellular organisms, such as viruses or parasites, are frequently resistant to drug therapy because of failure of the medicine to penetrate the cells. Other examples include the inability of AZT to penetrate the immune cell in the treatment of AIDS, the difficulty in treating another viral ailment, cytomegalic inclusion disease, and Chagas disease, a parasitic infestation.

While electrodes have been used to generate sufficient electromagnetic fields for electroporosis near the surface, they can not effectively reach tumors deep within the human body. Electrodes can easily be used when the tumor is superficial. However, electrodes require surgical procedures if they are to be used within the body.

U.S. Pat. No. 5,386,837 teaches a method of applying pulses of high-frequency force fields (rf, microwave, high-energy infrared, or laser electromagentic, or ultrasonic acoustic wave energy) to portions of the human body for the purpose of making those portions more susceptible to chemotherapeutic drugs. One or more applicators deliver energy such that at the site at which these beams intersect, the intensity is sufficient to open the cell. The '837 patent differs from this invention in several ways. The cited patent uses heat inducing sources. The present invention uses ultra-wide band (UWB) sources that are polarized time domain pulses that locally raise the field strength in the region of a tumor to a level sufficient to induce electroporosis. The use of UWB pulses also inherently provides for very low rf energy being used to induce electroporosis, the energy being limited to that associated with short pulses on the order of picoseconds to nanoseconds. This avoids tissue heating. The use of UWB pulses at a very low pulse repetition frequency also avoids osmotic shock, the rupture of cells when exposed to high field strength or too much exposure. Holding the cell walls open can result in an inability to close the pore and results in cell rupture.

SUMMARY OF THE INVENTION

The present invention overcomes the deficiencies of the prior art by providing both method and apparatus for treating tumors deep within the human body. Electroporosis is induced within a portion of the body through the use of an ultra-wide band pulser-driven transmission line or antenna. Chemotherapy can be applied either orally, by venous injection, or by local injection into the tumor via arterial catheter, in some cases enclosed within microscopic casings that open in high fields.

It is, therefore, an object of the present invention to provide an enhanced treatment for inoperable cancers by providing devices and associated techniques for the improved delivery of chemotherapeutic drugs to the diseased cells.

It is another object of the present invention to improve the delivery of chemotherapeutic drugs to cells in the case of diseases other than cancer, such as viral or parasitic infections.

It is a further object of the present invention to improve the ability to perform medical cellular research by increasing the ability to deliver therapeutic drugs directly into the cell interior.

DESCRIPTION OF THE PREFERRED EMBODIMENT

Chemotherapy, ionizing radiation, or the combination of radiation and chemotherapeutic modalities are frequently used to treat inoperable cancers. The chemotherapeutic effectiveness is limited by the inability of the chemical agent to penetrate into the tumor tissue and especially into the tumor cell. The present invention proposes to engender electroporosis in tumors deep within the human body that are not reachable by electrode techniques.

Figure 1:
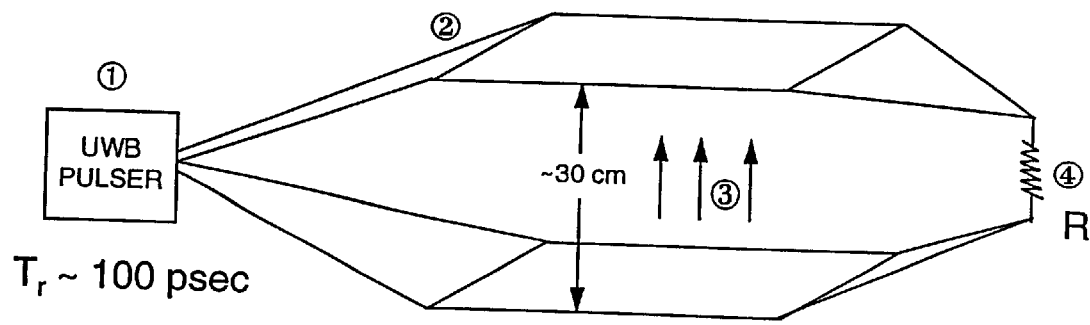
FIG. 1 shows a parallel plate transmission line driven by a UWB pulser.

The first embodiment of the present invention is shown in FIG. 1. This consists of a parallel plate transmission line 2 driven at one end by an ultra-wideband (UWB) high-power microwave pulser 1 featuring very fast rise time pulses. The other end of the line consists of a terminating resister 4 having a resistance equal to the characteristic impedance of the transmission line. The parallel plate transmission line has about a 30-cm aperture to admit the patient. The pulsed line 2 is covered with an insulator to prevent shocking the patient. The rise time of the UWB pulser is on the order of 100 picoseconds (ps). The peak field strengths in the high field region 3 obtained are in the range of 10–100 kilovolts per meter (kV/m) and pulse lengths are on the order of nanoseconds (ns) to a few microseconds ($\mu$s). The electric field of the UWB pulse is oriented vertically. The patient is introduced into the region between the transmission line plates so that the tumor is in the high field region.

Chemotherapy is administered in one of three ways. The chemical or drug can be administered orally in a manner such that a maximum chemical exposure baths the tumor at the time of the electromagnetic exposure, typically about 20 minutes after ingestion. A second option that in most cases is preferred over oral administration has the drug placed into the patient by injection into the brachial or femoral vein. In this case, circulation time to the tumor surface will be approximately a few minutes and high local transient concentrations will be achieved. The most desirable approach would employ catheterization of a tumor vessel and direct local exposure of the tumor to a chemical agent while the tumor is receiving the pulsed electromagnetic field.

Thus, the application of the electromagnetic could be about 20 minutes after the oral administration of a chemical agent, one to five minutes after the intravenous injection of a chemical, or simultaneous with the catheter delivery of the chemical. The electromagnetic treatment is envisaged to last 20 minutes with repeated pulsing to take advantage of chemical diffusion times and the time during which a cell membrane pore will remain open after formation by an electromagnetic field. The pulse repetition frequency (PRF) need be no more than needed to open the cell pores occasionally to admit the chemotherapeutic agent. The low pulse repetition frequency allows the cells to open pores and close them, while the combination of a low PRF and short pulses minimizes the patient's exposure to rf energy. A typical pulse repetition frequency would be a pulse every two minutes or a range of 0.1 to 0.001 Hz.

A novel but as yet unproved delivery means is that developed by Dr. Robert Liburdy of Lawrence Livermore Laboratories. He produced microscopic lipid saccules that carry chemotherapeutic agents and rupture in high peak electromagnetic fields, thus delivering high local concentrations of agents. This technique would benefit both from the action of the pulsed electromagnetic field for the purpose of releasing the agent in the vicinity of the tumor and also by enhancing penetration of the agent and its tumor killing effectiveness.

Figure 2:
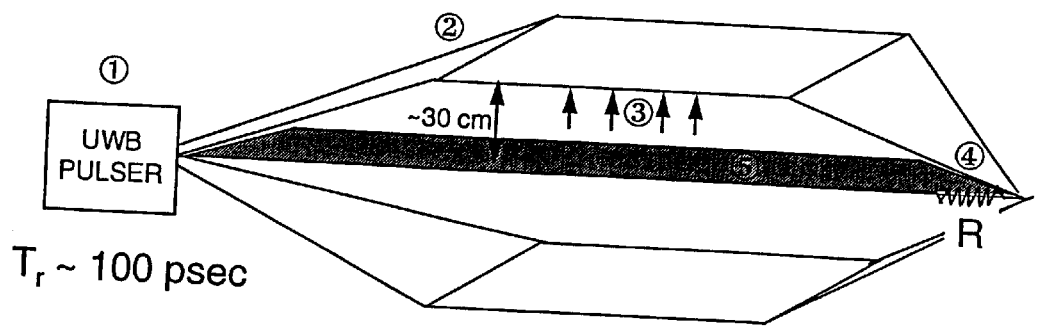
FIG. 2 is a parallel plate transmission line with a center conductor that is pulsed relative to the upper and lower conductors.

In FIG. 2 a Crawford cell type parallel plate transmission line 2 is shown. A pulser 1 provides voltage sufficient to generate 10–100 kV/m fields in region 3. The transmission line ends in a terminating resister 4 with a resistance equal to the characteristic impedance of the line. A center conductor 5 is pulsed relative to the upper and lower conductors. The transient electric field pulse is polarized with the electric field vertical. The patient or portion thereof is admitted between the center conductor and the upper transmission line, such that the tumor is more or less centered within the high field region 3.

Figure 3:
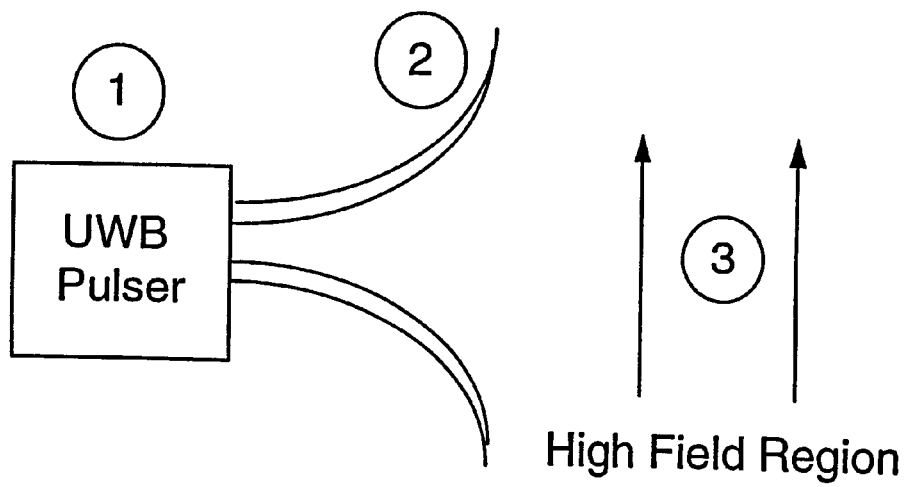
FIG. 3 shows a radiation UWB pulser and antenna system.

FIG. 3 shows another embodiment of the present invention. It consists of a radiating UWB pulser 1 in which a TEM horn antenna 2 is driven by a UWB pulser to produce UWB field in the high field region 3. The UWB pulser operates at sufficient voltage to generate peak field strengths of 10–100 kV/m in the high field region. The patient is introduced into the high field region 3 for treatment such that the patient's tumor is in the peak field region.

Figure 4:
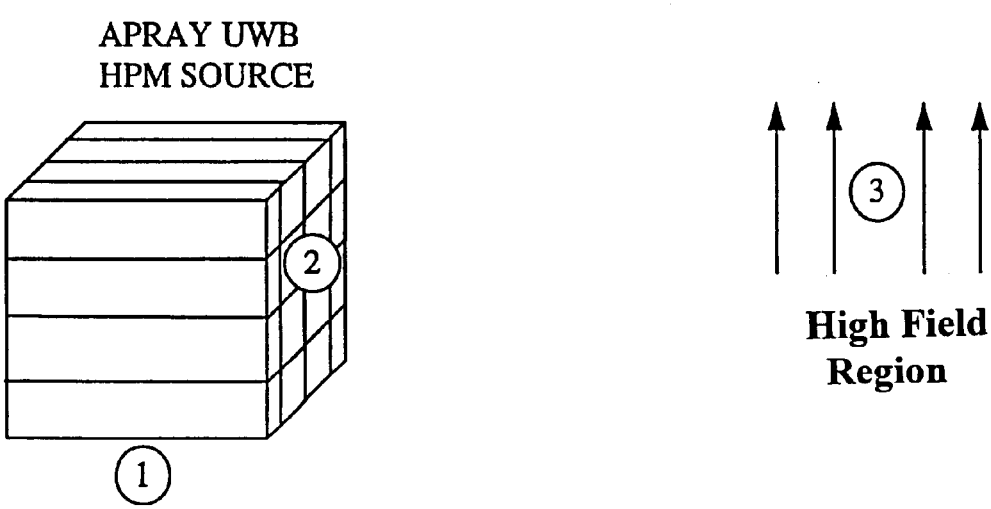
FIG. 4 shows a narrow beam impulse radiating antenna driven by an UWB pulser.

FIG. 4 shows another embodiment of the present invention. It uses an UWB pulser 1 narrow beam impulse radiating antenna (IRA) 2 with a beam width on the order of 1° to focus the UWB energy onto the area to be treated 3.

The techniques described herein generate sufficient electromagnetic fields to permit electroporosis of deep-seated internal tumors. Electroporosis can thereby be induced in the tumor preferentially over other parts of the body. A further benefit is that the need for contact with the skin by electrodes is eliminated. This is important when treating painful cancers, such as cancer of the pancreas, where even wearing normal clothing can be painful.

The use of linearly polarized, short pulses makes the thermal heating associated with other microwave sources negligible, and it avoids wholesale damage of cells by enabling the cells to open pores and then close them. The disclosed techniques increase the amount of chemical agent absorbed in the desired region while reducing the total dose of agent required to treat the patient. Higher local doses to the cancer substantively increase the probability of cure. The lower total doses to the body as a whole reduce chemical side effects.

This invention will potentially increase the range and type of cancers that can be treated by chemotherapy. It will allow treatment of certain cancers that cannot now be effectively treated by surgery, radiation, chemotherapy, or combinations of these modalities, e.g., glioblastoma multi forme. Additional specific cancer targets include, but are not restricted to, cancer in the tail of the pancreas, hepatocarcinoma, and nonresectable colonic adenocarcinoma.

It will be apparent that many modifications and variations may be implemented without departing from the scope of the novel concept of this invention. Therefore, it is intended by the appended claims to cover all such modifications and variations which fall within the true spirit and scope of the invention.

What is claimed is:

1. A parallel plate transmission line apparatus for use in an electroporosis treatment providing a required 10 to 100 kV/m high field region, said apparatus comprised of:
   a) an insulated parallel plate transmission line having an upper plate, a lower plate, a first end, and a second end and being of sufficient size to position a body between said upper and lower plates;
   b) an ultra-wide band pulser connected to the first end of said parallel plate transmission line and capable of providing sufficient voltage to generate 10 to 100 kV/m electromagnetic fields in the high field region between the upper and lower plates of said parallel plate transmission line;
   c) a terminating resister connecting to the upper and lower plates at said second end with a resistance approximately equal to the characteristic impedance of said parallel plate transmission line.

2. The apparatus of claim 1, wherein the pulses of the ultra-wide band pulser have a rise time on the order of 100 picoseconds.

3. The apparatus of claim 2, wherein the pulse lengths are on the order of nanoseconds to microseconds.

4. The apparatus of claim 1, wherein the parallel plate transmission line is a Crawford cell having a center conductor that is pulsed by said ultra-wide band pulser and said Crawford cell having sufficient dimensions to admit a body between said center conductor and said upper plate.

* * * * *